United States Patent
Diamant et al.

(10) Patent No.: US 8,926,630 B2
(45) Date of Patent: *Jan. 6, 2015

(54) DEVICE AND METHOD FOR FRAGMENTING AND REMOVING CONCRETIONS FROM BODY DUCTS AND CAVITIES

(71) Applicant: Lithotech Medical Ltd., Katzrin (IL)

(72) Inventors: Valery Diamant, Katzrin (IL); Nadezda Yasko, Tomsk (RU); Aleksei Dutov, Tomsk (RU); Vladimir Chernenko, Tomsk (RU); Marat Lerner, Tomsk (RU)

(73) Assignee: Lithotech Medical Ltd., Katzrin (IL)

( * ) Notice: Subject to any disclaimer, the term of this patent is extended or adjusted under 35 U.S.C. 154(b) by 99 days.

This patent is subject to a terminal disclaimer.

(21) Appl. No.: 13/682,133

(22) Filed: Nov. 20, 2012

(65) Prior Publication Data

US 2013/0079797 A1    Mar. 28, 2013

Related U.S. Application Data

(63) Continuation of application No. 12/778,273, filed on May 12, 2010, now Pat. No. 8,328,820, which is a continuation of application No. PCT/IL2008/001508, filed on Nov. 17, 2008.

(30) Foreign Application Priority Data

Dec. 12, 2007 (IL) .......................................... 188067

(51) Int. Cl.
*A61B 17/22* (2006.01)
*A61B 17/221* (2006.01)
*A61B 17/32* (2006.01)
*A61B 17/3203* (2006.01)
*A61B 18/26* (2006.01)
*A61B 17/00* (2006.01)
*A61B 17/92* (2006.01)

(52) U.S. Cl.
CPC ..... *A61B 17/22022* (2013.01); *A61B 17/22012* (2013.01); *A61B 17/221* (2013.01); *A61B 17/32002* (2013.01); *A61B 17/3203* (2013.01); *A61B 18/26* (2013.01); *A61B 2017/00867* (2013.01); *A61B 2017/00915* (2013.01); *A61B 2017/2215* (2013.01); *A61B 2017/320072* (2013.01); *A61B 2017/922* (2013.01)
USPC ............................................. 606/128; 606/2.5

(58) Field of Classification Search
CPC ........... A61B 17/221; A61B 17/22032; A61B 17/32056
USPC .................................. 606/113, 114, 127, 128
See application file for complete search history.

(56) References Cited

U.S. PATENT DOCUMENTS 5,330,482 A     7/1994  Gibbs et al.
6,264,664 B1 *  7/2001  Avellanet ...................... 606/128

(Continued)

*Primary Examiner* — Tuan V Nguyen
(74) *Attorney, Agent, or Firm* — Browdy and Neimark, PLLC

(57) ABSTRACT

A medical device and method for breaking a concretion in a body into smaller pieces and removing the pieces from the body are described. The device comprises a dilator sheath, a lithotripsy probe, a tubular member, and a retrieval basket. The dilator sheath adapted to penetrate into a passage of the body to reach the location where the concretion is located. The lithotripsy probe is configured for shattering the concretion into smaller pieces. The tubular member is mounted within the dilator sheath adapted to permit the lithotripsy probe to be inserted into the tubular member. The retrieval basket is coupled to the tubular member, and configured for entrapping the concretion and the smaller pieces for their extraction from the body. The retrieval basket comprises a structure constituted by a plurality of filaments extending from a basket proximal end towards a basket distal end, and then returning to the proximal end after forming a plurality of filament loops in the basket distal portion, and a plurality of filament strands at the basket proximal portion.

20 Claims, 11 Drawing Sheets

(56) References Cited

U.S. PATENT DOCUMENTS

| | | |
|---|---|---|
| 6,280,451 B1 | 8/2001 | Bates et al. |
| 6,350,266 B1 | 2/2002 | White et al. |
| 6,500,182 B2 * | 12/2002 | Foster .......................... 606/127 |
| 7,101,380 B2 | 9/2006 | Khachin et al. |
| 7,377,925 B2 | 5/2008 | Poll |
| 7,824,415 B2 | 11/2010 | Teague et al. |
| 8,328,820 B2 * | 12/2012 | Diamant et al. .............. 606/128 |
| 2003/0176873 A1 | 9/2003 | Chernenko et al. |
| 2006/0129166 A1 | 6/2006 | Lavelle |
| 2008/0086149 A1 | 4/2008 | Diamant et al. |

* cited by examiner

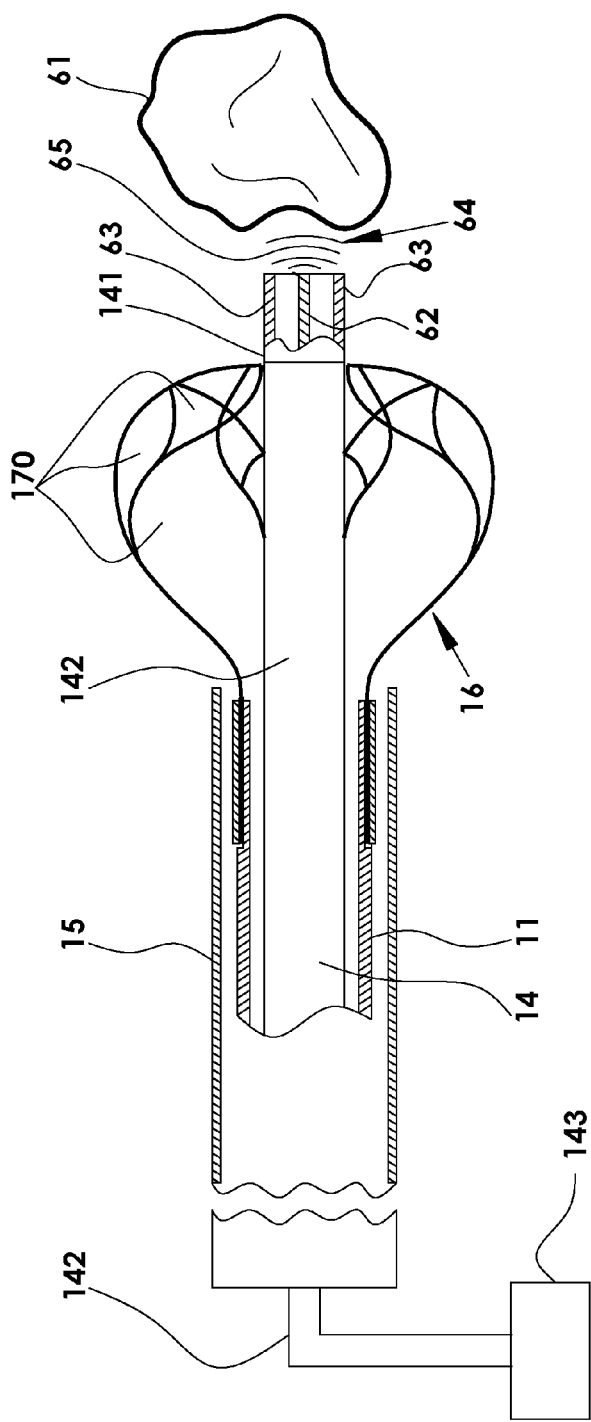
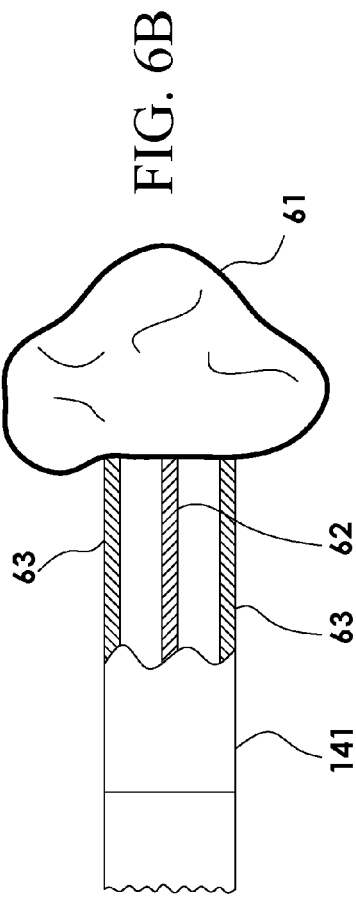
FIG. 6A
FIG. 6B

DEVICE AND METHOD FOR FRAGMENTING AND REMOVING CONCRETIONS FROM BODY DUCTS AND CAVITIES

FIELD OF THE INVENTION

This invention relates to a device and method for fragmenting abnormal concretions and extracting their pieces from hollow bodies, and in particular, to a medical instrument for fragmenting and removing solid calculous formations from the ducts and cavities of a living body.

BACKGROUND OF THE INVENTION

Several techniques are employed in clinical practice for breaking abnormal concretions appearing in the biliary and/or urinary system of a human body into pieces for further removal of the pieces from the body. The term "concretion" as used herein refers to solid calculous formations of urates, oxalates and phosphates, e.g. gallstones, kidney stones, cystine stones and other calculi, lodged in the ducts and cavities of a living body. Although procedures have varied, most of them have involved dilatating, anesthetizing and lubricating the urinary or biliary tract, and then attempting to grasp the calculus for crushing it, and then dragging it out.

For example, extra- and intra-corporeal shock wave lithotripsy is widely used which employs high-energy shock waves to fragment and disintegrate calculi. In extracorporeal shock-wave lithotripsy, an energy needed for stone fragmentation, in the form of shock waves, is transferred from an outside source through body tissue to the calculi. In turn, intra-corporeal shock wave lithotripsy utilizes a probe advanced with the aim of an endoscope and positioned in proximity to the calculus. The shock waves, required for fragmentation, are transferred through the probe to the calculus, and the treatment process can be visualized during fragmentation.

Ultrasonic lithotripsy technique is known that utilizes an ultrasound probe emitting high-frequency ultrasonic energy towards a concretion. For this technique, direct contact of the probe tip and stone is essential for effectiveness of ultrasonic lithotripsy.

Lasers are known as an alternative source of energy in lithotripsy, especially for the destruction of renal and biliary stones. Various types of laser lithotripsy probes with a variety of laser sources, including pulsed dye laser, alexandrite laser, neodymium laser, holmium laser and other lasers, have been developed.

Electrohydraulic lithotripsy (EHL) has been an accepted form of therapy for the destruction of urinary stones both in the human bladder and within the individual ureters. EHL is extremely effective in breaking large urinary stones into pieces small enough for basket extraction or simple passage. When EHL is selected to affect the destruction of the stone, the EHL probe is placed in proximity to the stone. By means of an electrical discharge, a shock wave is produced which impacts the surface of the stone and produces tiny cracks. When enough cracks have been made, the stone shatters into small pieces. The individual pieces can then be attacked one at a time, or they can further be removed by basket extraction.

A lithotripsy technique of electro-impulse destruction of materials is also known in the art (see, for example, U.S. Pat. No. 7,087,061 to Chernenko, et al). Contrary to electrohydraulic destruction, employing electrodes which are not in direct contact with the object, electro-impulse destruction utilizes a probe with electrodes which are placed directly on the object's surface. This technique is based on the Vorob'evs effect that provides certain features of the discharge observed when a solid dielectric in contact with two rodlike electrodes is placed in a liquid dielectric medium, and a voltage pulse with increasing front is applied to the electrodes. According to this effect, when the pulse front slope is small (e.g., the pulse rise time is more than about 0.5 microseconds), the discharge develops in the surrounding liquid over the solid dielectric surface rather than penetrating into the solid body. On the other hand, in the case of a sufficiently large slope of the pulse front, the discharge propagates through the solid and produces its fracture with cleavage of the surface fragments (see, for example, G. A. Masyats, *Technical Physics Letters*, Vol. 31, No. 12, 2005, pp. 1061-1064. Translated from Russian from *Pis'ma v Zhurnal Tekhnicheskoi Fiziki*, Vol. 31, No. 24, 2005, pp. 51-59).

A problem associated with lithotripsy probes is that the calculi are not captured during treatment. For example, a stone can be pushed along the ureter towards the kidney in response to efforts to treat it. Likewise, the stone can also move to the side of the catheter and wedge between the ureter wall and the catheter.

There are known medical devices combining a lithotripsy probe used to break calculi with a retrieval collapsible wire basket that allows a secure hold on a urinary or biliary stone, while the destructive forces of the lithotripsy probe are used to shatter the stone. One of the advantages of such combined lithotripsy devices is in the fact that the operator using such a device is not required to change a lithotripsy probe and a retrieval basket in the middle of the procedure, within the very restrictive confines of the urinary or biliary tract.

For example, U.S. Pat. No. 5,176,688 to Narayan, et al. describes a stone extractor and method in which a stone is captured in a retrieval basket at the distal end of an elongated tubular member and broken into pieces while it is held by the basket. The stone is broken up by a reciprocating shaft which extends through the tubular member into the basket and is driven toward the stone by a spring to provide an effective hammering action without injuring the surrounding tissue. The stone is removed from the body by withdrawing the tubular member from the body with the pieces of the stone in the basket.

U.S. Pat. No. 5,397,320 to Mitchell, et al. describes a laparoscopic surgical device which comprises an elongated shaft having a plurality of electrically conductive flexible ribs connected to the distal end of the shaft and to one another to form a cage or basket. Upon placement of an organic body in the cage, the ribs are electrically energized. The organic body is pressed against the ribs to dissect the ribs in a single cauterization operation.

U.S. Pat. No. 6,319,261 to Bowers describes a combination lithotripsy device for the destruction of calculi such as urinary stones in the human bladder, individual urinary ureters, the biliary tract, or other locations in the human body. More specifically, the device includes an electrohydraulic probe combined with a basket which consists of multiple electrical conduit wires that act both as electrical conduits and collectively act as a grasping device.

SUMMARY OF THE INVENTION

There is a need in the art for, and it would be useful to have a novel medical device combining lithotriptic and retrieval features, which is capable to be safely introduced into the confined space of the individual ureter, urinary bladder or biliary tract, to secure the concretion, shatter the concretion into smaller pieces, and retrieve the pieces from the body tracts.

It would also be advantageous to have a method for destruction and removal of the concretion utilizing the device of the present invention.

The present invention satisfies the aforementioned need by providing a novel medical device for entrapping concretions in ducts and cavities of a living body, breaking them into smaller pieces and removing the pieces from the body. The medical device includes a dilator sheath, a lithotripsy probe, a tubular member mounted within the dilator sheath and accommodating the lithotripsy probe, and a retrieval basket coupled to the tubular member.

The dilator sheath is adapted to penetrate into a passage of the body to reach the location where the concretion to be shattered into smaller pieces is located. The lithotripsy probe is configured for shattering the concretion into smaller pieces. The tubular member has a proximal member end, a distal member end and an axially extending inner lumen provided within the tubular member to permit the lithotripsy probe to be inserted into the tubular member from the proximal end. The retrieval basket is configured for entrapping and retaining the concretion and the smaller pieces for their extraction from the body. It should be noted that in the description and claims that follow, the terms "proximal" and "distal" are used with reference to the operator of the medical device.

The retrieval basket comprises a structure that has a basket proximal portion and a basket distal portion. The structure is constituted by a plurality of filaments extending from a basket proximal end towards a basket distal end, and then returning to the proximal end after forming a plurality of filament loops in the basket distal portion, and a plurality of filament strands at the basket proximal portion. The sides of the filament loops are connected to the sides of adjacent loops at the distal portion of the basket to form a net defining a distal opening at the basket distal end and a plurality of side openings along the structure of the basket. The distal opening in the basket has such dimension so that to permit the lithotripsy probe to protrude through the distal opening.

According to an embodiment of the present invention, the connection of the loops is achieved by twisting the filaments forming the corresponding sides of the adjacent loops by at least one turn.

The filaments forming the structure of the basket can be either single-core wires or multiwire strands.

According to one embodiment of the present invention, the filaments forming the structure of the basket are made of a metallic material having super elastic and thermo-mechanical shape memory characteristics. For example, the metallic material can be a NiTi based alloy. Likewise, the metallic material can be stainless steel.

When desired, the metallic material can include a radiopaque material. The radiopaque material can, for example, be at least one of the following metals: Pt, Au, Ag, Pd, W, Nb, Co, and Cu.

According to another embodiment of the present invention, the filaments can be made of a core tube containing an axially disposed radiopaque wire.

According to a further embodiment of the present invention, the medical device can comprise one or more radiopaque markers attached to one or more loops.

When the filaments forming the structure of the basket are multiwire strands, they can include a central core wire and at least one another wire twisted about the central core wire. When desired, such another wire is made of a material having a level of radiopacity greater than the level of radiopacity of the central core wire.

According to yet a further embodiment of the present invention, the filaments are made of non-metallic material. Examples of the non-metallic material include, but are not limited to, Capron and Nylon.

According to an embodiment of the present invention, the dilator sheath is made of a flexible strong material that can, for example, be a plastic material or a composite material. The tubular member is a deflectable tube. Examples of materials suitable for the tubular member include, but are not limited to, polyimide, nylon, and polyester.

According to an embodiment of the present invention, the tubular member distal end has a hollowed-out portion for connecting the tubular member to the filament strands of the retrieval basket along the surface circumference of the hollowed-out portion.

According to an embodiment of the present invention, the medical device comprises a tube put on the filament strands at the hollowed-out portion. Preferably, but not mandatory, the tube is made of a thermo-shrinkable material.

Examples of the lithotripsy probe include, but are not limited to, an electro-hydraulic lithotripsy probe, an electro-impulse lithotripsy probe, an ultrasonic wave lithotripsy probe, a mechanic lithotripsy probe, and a laser light lithotripsy probe.

The aforementioned need is also satisfied by providing a method for breaking a concretion in a body it into smaller pieces and removing the pieces from the body by using a medical device of the present invention.

A particular order of the method steps depends on the size of a concretion. When the concretion is smaller than the side openings in the structure of the basket, the concretion can first be captured by the basket and immobilized therein. The entrapped concretion can be shattered into pieces. In this case, the method includes the steps of:

(a) inserting the medical device in a basket closed position through an endoscope into the body into proximity with the concretion;

(b) manipulating the tubular member and the dilator sheath for opening the retrieval basket, entrapping the concretion in the retrieval basket, and closing the basket around the concretion;

(c) manipulating the lithotripsy probe for protruding thereof from the lumen in the tubular member and bringing thereof into proximity with the concretion entrapped in the retrieval basket;

(d) energizing the lithotripsy probe to cause the concretion to break into smaller pieces; and (e) removing the medical device from the body together with at least one piece of the concretion immobilized within the basket.

On the other hand, when the concretion is relatively large, and cannot pass through the side openings in the structure of the basket, the concretion should first be shattered into pieces by using the lithotripsy probe. In this case, the method includes the steps of:

(a) inserting the medical device in a basket closed position through an endoscope into the body into proximity with the concretion;

(b) manipulating the lithotripsy probe for protruding thereof from the lumen in the tubular member and the distal opening of the basket to bring the lithotripsy probe into proximity with the concretion entrapped in the retrieval basket;

(c) energizing the lithotripsy probe to cause the concretion to break into smaller pieces;

(d) manipulating the tubular member and the dilator sheath for opening the retrieval basket, entrapping at least one piece of the concretion in the retrieval basket, and closing the basket around the piece; and (e) removing the medical device from the body together with the piece of the concretion immobilized within the basket.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 6A illustrates schematically the juxtaposition of the concretion and the impact tip of the electro-hydraulic lithotripsy probe;

FIG. 6B illustrates schematically the juxtaposition of the concretion and the impact tip of the electro-impulse lithotripsy;

DETAILED DESCRIPTION OF EXEMPLARY EMBODIMENTS

Figure 1:
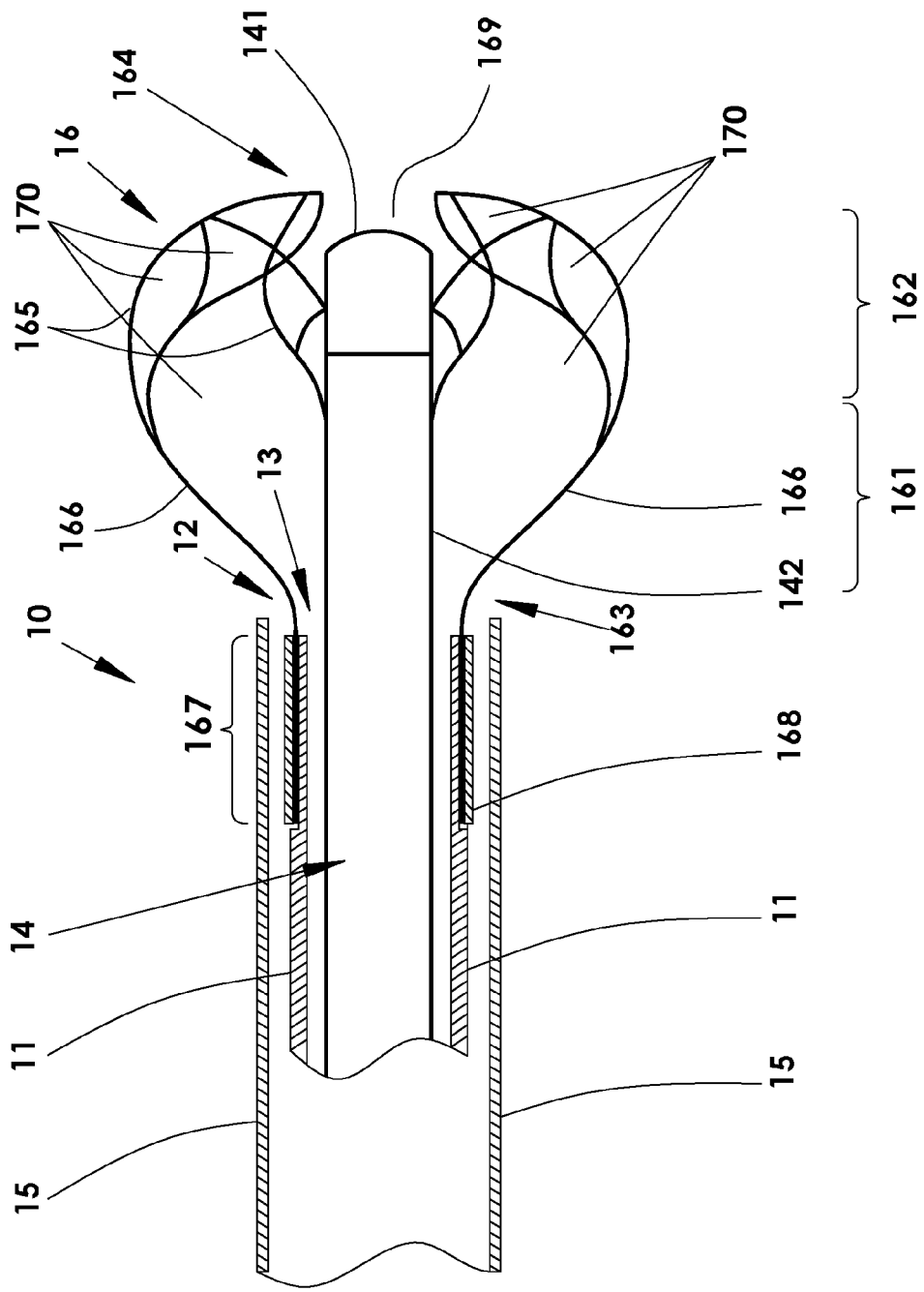
FIG. 1 is a schematic side cross-sectional view of a distal portion of a medical device in a deployed position, according to one embodiment of the present invention.

The principles of the method for the medical device according to the present invention may be better understood with reference to the drawings and the accompanying description, wherein like reference numerals have been used throughout to designate identical elements. It being understood that these drawings which are not necessarily to scale, are given for illustrative purposes only and are not intended to limit the scope of the invention. Examples of constructions, materials, dimensions, and manufacturing processes are provided for selected elements. Those versed in the art should appreciate that many of the examples provided have suitable alternatives which may be utilized.

FIG. 1 illustrates a schematic side cross-sectional view of a distal portion of a medical device 10 in a deployed position, according to one embodiment of the present invention. The medical device 10 includes an elongated, catheter-like tubular member 11 which has a tubular member proximal end (not shown), a tubular member distal end 12 and an axially extending inner lumen 13 provided within the tubular member 11 to permit a lithotripsy probe 14 to be inserted into the tubular member 11 from the proximal end. The tubular member 11 is a deflectable tube fabricated of a relatively stiff yet somewhat pliant material, which permits the device to be introduced into a patient's body (not shown) along a tortuous path. Examples of materials suitable for the tubular member 11 include, but are not limited to, polyimide, nylon, polyester, etc.

The lithotripsy probe 14 is mounted within the inner lumen 13 so that it may be extended or retracted by an operator (not shown). It should be noted that the present invention is not limited to a specific kind of lithotripsy technique for breaking concretions. Generally, the lithotripsy probe 14 includes an impact tip 141, a control cable (rod) 142 coupled to the tip 141, and an energy unit (not shown) coupled to the control cable 142. In operation, the impact tip 141 is placed against the concretions, e.g., stone, (not shown) and the energy unit is activated to provide energy sufficient for breaking the stone into much smaller fragments. Various types of the lithotripsy probe 14 suitable for the purpose of the present invention will be described more fully below in connection with FIGS. 6A, 6B, 7, 8 and 9.

The medical device 10 further includes a dilator sheath 15 formed as a tubular catheter. The dilator sheath 15 is a thin-walled, cylindrical flexible tube adapted to penetrate into a body passage (not shown) to reach the location where the concretion to be shattered into smaller pieces, is located. The catheter-like tubular member 11 is mounted within the dilator sheath 15, and can be manipulated by the operator from the outside at the sheath's proximal end (not shown). For example, the dilator sheath 15 can be made of a flexible, durable, strong plastic material, such as polyimide, polyvinyl chloride, nylon, teflon, etc. The dilator sheath 15 can also be made of a composite material, such as a wire mesh or a coil, (e.g., stainless steel coil). When desired, the sheath 15 may be multi-layered with different materials in order to provide a graduated bending and stiffness characteristic over its length.

The medical device 10 further includes a retrieval basket 16 coupled to the catheter-like tubular member 11 at the tubular member distal end 12. The retrieval basket 16 is used in a ureter, urinary bladder or biliary tract (not shown) to trap the concretion that can be shattered into smaller pieces by the lithotripsy probe 14, and to retrieve the pieces from the body tracts.

A plan view of the retrieval basket 16 in a deployed (opened) position is illustrated in FIG. 1, according to one embodiment of the present invention. In general, the structure of the retrieval basket 16 comprises a proximal portion 161 and a distal portion 162, and is constituted by a plurality of filaments fabricated from one or more wires that extend from a basket proximal end 163 towards a basket distal end 164 and then return after winding to the proximal end 163 to form a plurality of filament loops 165. After forming the loops in the distal portion 162, the filaments are bound together in filament strands 166 at the proximal portion 161 of the basket.

According to one embodiment of the invention, each filament forming the structure of the basket is a single-core wire. According to another embodiment of the invention, each filament is a multi-wire strand.

The filaments of the retrieval basket 16 can each have a cross-sectional diameter in the range of from about 0.05 mm to about 0.15 mm. The diameters of the filaments may vary from wire-to-wire and/or along the lengths of each wire.

The filaments utilized for the fabrication of the retrieval basket 16 are made of a suitable material that is suitably biocompatible and has thermo-mechanical shape memory and/or superelastic properties. According to one embodiment of the invention, the filaments are made of a metallic material. For example, the metallic material can be selected from a NiTi based alloy (e.g., Nitinol), stainless steel and other materials possessing good shape memory, elastic or superelastic characteristics. According to another embodiment of the invention, the filaments are made of non-metallic material, e.g. Capron, Nylon, etc.

According to a still further embodiment of the invention, the filaments of the basket are covered by an insulating layer. The insulating layer can, for example, be made of Teflon. The advantage of Teflon is its thermal resistance and low coefficient of mechanical friction, which leads to an additional reduction of traumatism.

Preferably, but not mandatory, the filaments are radiopaque, so as to permit them to be visualized by a fluoroscope with respect to the object to be retracted. Thus, according to one example, in order to provide radiopacity, the metallic material from which the filaments are made can include a material which provides radiopacity, e.g., a noble metal, such as gold, tantalum, platinum, etc. Likewise, the metallic material can be alloyed with one or more metals selected from Pd, W, Nb, Co, Cu, etc.

According to another example, the filaments are made of a core tube (cannular strand) containing an axially disposed radiopaque wire.

According to yet another example, the filaments can have radiopaque parts of a predetermined length. These radiopaque parts can form the distal portion 162 of the basket or at least a part of the distal portion.

Radiopacity can also be improved through coating processes such as sputtering or plating a radiopaque material onto the filaments, or the basket fabricated from these filaments, thereby to provide a radiopaque coating layer on the filaments.

Likewise, radiopacity can yet be improved by using radiopaque markers (not shown) which can be attached to or placed around the filaments forming the basket. In this manner, materials which have higher radiopacity than the basket structure itself, such as gold, tantalum or platinum, can be utilized as markers and be strategically placed along the body of the basket to increase the visualization of the basket. For example, the retrieval basket can comprise one or more radiopaque markers (not shown) attached to or placed around the filaments forming one or more filament loops 165 in the distal portion 162. For example, the radiopaque marker can be a ferrule put on the filament.

According to another embodiment of the invention, the filaments can be multi-wire strands. In such a case, in order to improve radiopacity, the multi-wire strands can include a central core wire and at least one another wire twisted about said central core wire which is made of a material having a level of radiopacity greater than the level of radiopacity of said central core wire. Examples of such a material include, but are not limited to, Pt, Au, Pd, Ta, etc.

According to one embodiment of the invention, each filament originates from a certain point at the basket proximal end 163, and extends towards the basket distal end 164 to form a loop. After forming the loop, the filament returns to the original point at the basket proximal end 163 to form one of the basket filament strands 166 in the proximal portion 161.

According to another embodiment of the invention, each filament extends from a certain point at the basket proximal end 163, and then, after enwinding with other filaments, arrives at another point at the basket proximal end 163, where the filaments meet with one or more other filaments. In this case, each filament strand 166 is formed by two or more different filaments that correspond to the sides of adjacent loops.

Description of various embodiments of the retrieval basket 16 of the medical device 10 will be described more fully below in connection with FIGS. 3-5.

At the basket proximal end 163, the filament strands 166 are connected to the catheter-like tubular member 11 along the surface circumference of the tubular member distal end 12. A joining portion 167 may, for example, be a hollowed-out portion at the distal end of the tubular member 11 (as shown in FIG. 1). The axial dimension of hollowed-out portion can, for example, be in the range of about 15 mm-25 mm. Alternatively, joining portion 167 can include a separate ferrule, such as a hollow cannula made of metal, e.g., stainless steel, etc.

The filaments from the basket strands 166 can be trimmed and coupled to the tubular member 11 along the surface circumference of the tubular member distal end 12 by one or more connecting means.

In one embodiment, the filament strands 166 of the retrieval basket can be directly connected to the tubular member 11. For instance, the filament strands 166 may be soldered, brazed or welded to the tubular member 11 at the joining portion 167. Likewise, a medically-acceptable adhesive may also be used to secure or join the filament strands 166 to the tubular member 11. An example of the adhesive includes, but is not limited to, LOCTITE® 4011 cyanoacrylate.

In order to increase mechanical strength, a thin tube 168 can be put on the filament strands 166 at the joining portion 167, as shown in FIG. 1. The tube 168 can be made of a thermo-shrinkable material. An example of the material suitable for the tube 168 includes but is not limited to Polytetrafluoroethylene (PTFE). The wall thickness of the tube 168 can, for example, be in the range of about 0.005 mm-0.01 mm.

In another embodiment, a separate ferrule (not shown), may be used to connect the filament strands 166 or loops to the tubular member 11. The ferrule can be joined to the tubular member 11 and to the filament strands, preferably, by soldering, welding or brazing, although other known techniques, such as gluing, may also be used. For instance, if soldering is used, the end of the tubular member 11 is first etched, preferably with acid, followed by neutralizing and drying. Flux is then applied to both the tubular member 11 and the cannula, the two are soldered together, and excess solder is removed. Afterwards, the parts should be neutralized, dried and cleaned.

At the distal portion 162 of the basket, the filament loops 165 are overlapped and/or interlaced with each other so as to form open spaces between the filaments. The filament loops 165 define a net that has a distal opening 169 at the basket distal end 164, and a plurality of side openings 170 along the basket's structure. Note that the term "overlapped" herein is assigned to such arrangement of the filaments forming the filament loops, in which one element crosses other filaments, i.e., one of the filaments always being over or under the other filaments. The term "interlaced" herein is assigned to the situation when at least one filament interweaves with the other filaments, i.e., one of the filaments passes first above the crossed filament and then passes under the next crossed filament.

The distal opening 169 in the basket has such dimension so as to permit the lithotripsy probe 14 to be protruded through the distal opening 169 in order to bring the probe 14 into proximity with the object (not shown), when it is located in front of the basket. This provision permits to apply destruction energy to relatively large concretions. A large concretion can only be located in front of the basket, because the concretion cannot pass through the side openings 170 to be captured and entrapped within the basket, owing to the big size of the concretion. After the breaking of such a concretion into parts, the smaller pieces can be captured and retained in the basket for their further destruction inside the basket, or removal from the patient's body.

The method for removing concretions within ducts and cavities of a living body according to the present invention involves the following steps. According to one embodiment of the present invention, an endoscope (not shown) steerable by an operator is first inserted into the patients body tract and/or cavity into proximity with the concretion by known means, for example, through a surgical incision, through the urethra or through any other duct. The endoscope can, for example, be a cystoscope, a urethroscope or another suitable device that includes both a light source and fiber optics so that the stone can be seen when the device is properly inserted. Thereafter, the medical device of the present invention is inserted through the endoscope into the body.

When a concretion is relatively large, and the basket cannot pass beyond the concretion for its capturing or it cannot pass through the side openings in the structure of the basket, the concretion should first be shattered into pieces by using the lithotripsy probe 14.

Figure 2A:
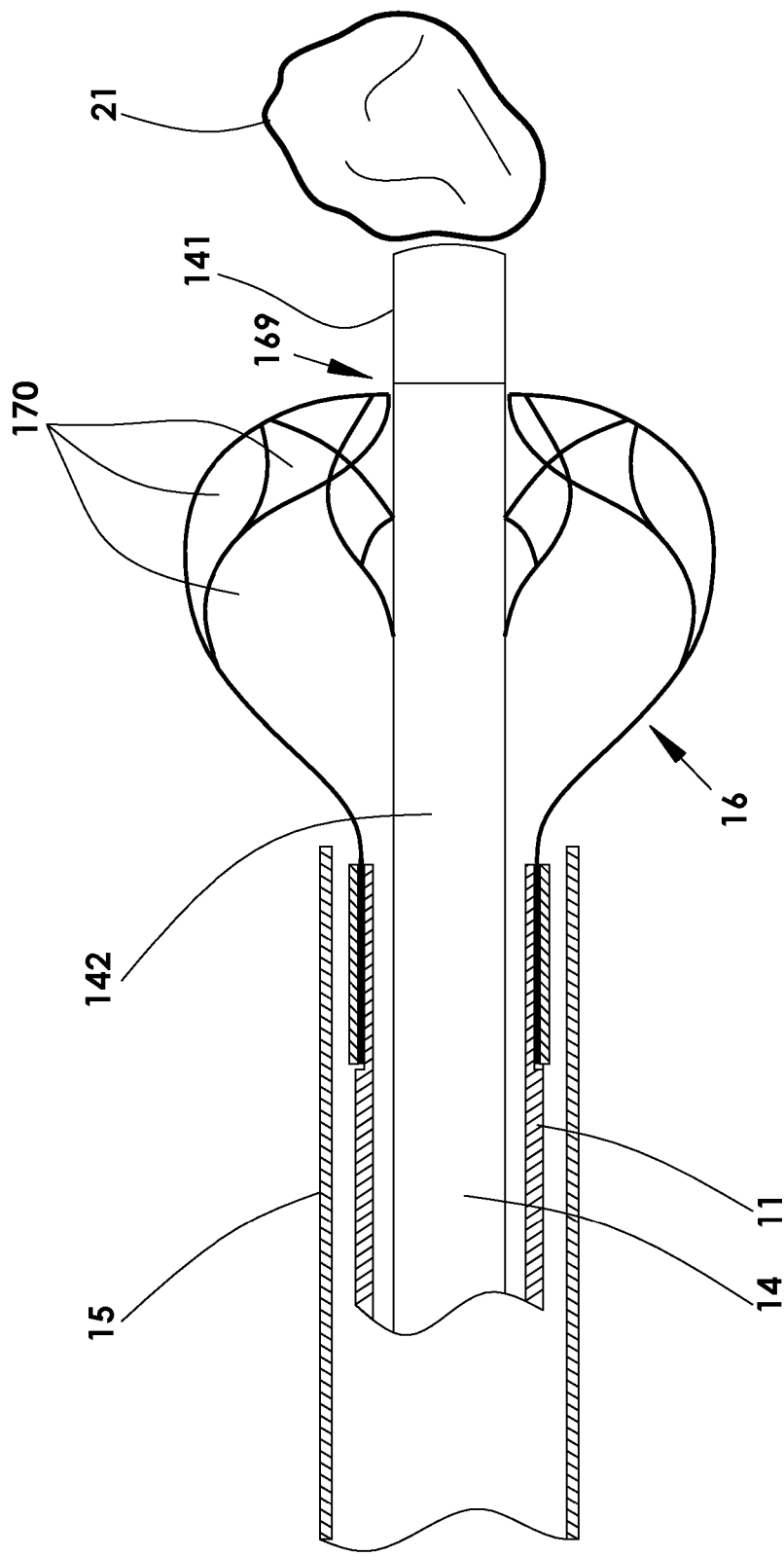
FIGS. 2A and 2B illustrate a schematic side elevational view, partially broken away, of a distal portion of the medical device shown in FIG. 1, showing a foreign object arranged in front of the retrieval basket being in an opened position and in a retracted position, correspondingly.
Figure 2B:
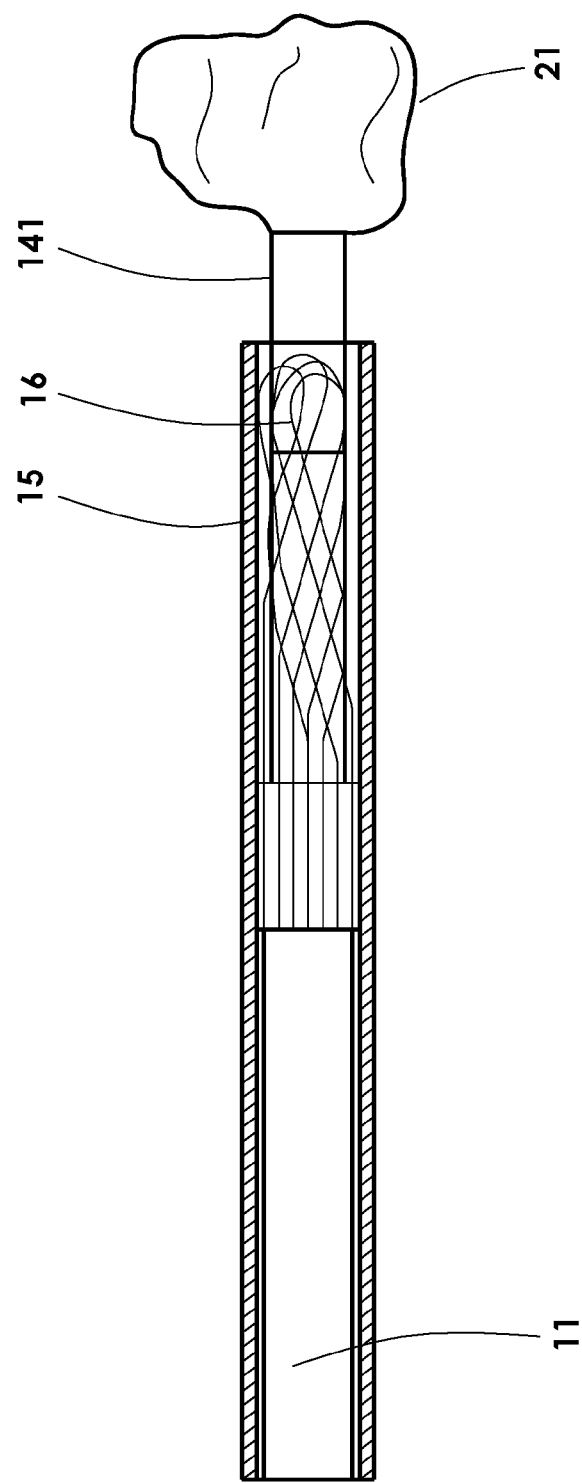

FIGS. 2A and 2B illustrate two examples of operation of the medical device shown in FIG. 1 when an object (concretion) 21 is arranged in front of the retrieval basket 16. It should be understood that when the object is arranged in front of the retrieval basket 16, in operation, the basket can be either open or closed. Specifically, when the basket is fully open, as shown in FIG. 2A, the opened basket 16 forms a cage to allow the pieces of the shattered object to enter into the side openings 170 left between the filaments. In order to shatter the object, the lithotripsy probe 14 can be protruded through the distal opening 169 for bringing the impact tip 141 into proximity with the object 21. Depending on the lithotripsy technique, the end of the impact tip 141 of the lithotripsy probe 14 can be close to, or in direct contact with a surface of the object 21.

Likewise, the basket 16 may only be partially opened or even be completely retracted inside the sheath 15. As shown in FIG. 2B, the lithotripsy probe 14 can be protruded through the distal opening 169 and brought into contact with the object, whereas the basket is located within the sheath 15.

After bringing the lithotripsy probe 14 into proximity with the object 21, the probe is energized for applying destruction energy to the object. After the shattering of the object into pieces, the basket can be advanced for opening and entrapping the pieces having smaller dimensions than the dimensions of the original object 21.

The retrieval basket 16 and the sheath 15 can move relative to each other to open and close the basket 16. Depending on the manipulation of the tubular member 11, the basket 16 may either retract inside the sheath 15, to allow penetration of the sheath 15 via a passage, or protract from the sheath 15. In the protracted position, the basket 16 is open, due to the elasticity of the filament material, and forms a cage to thus allow entry of an object (e.g., concretion) inside the basket through the open spaces left between its adjacent filaments. Further retraction of the basket 16 inside the sheath 15 results in the cage collapsing and entrapping the object in the basket.

When the object is relatively small, distal end portion of the basket is moved slightly beyond the stone to be removed. Then, the basket is opened, and the instrument is manipulated to capture the concretion in the basket. Once the concretion has been captured, the basket is closed around the concretion to retain the concretion in the basket.

Figure 2C:
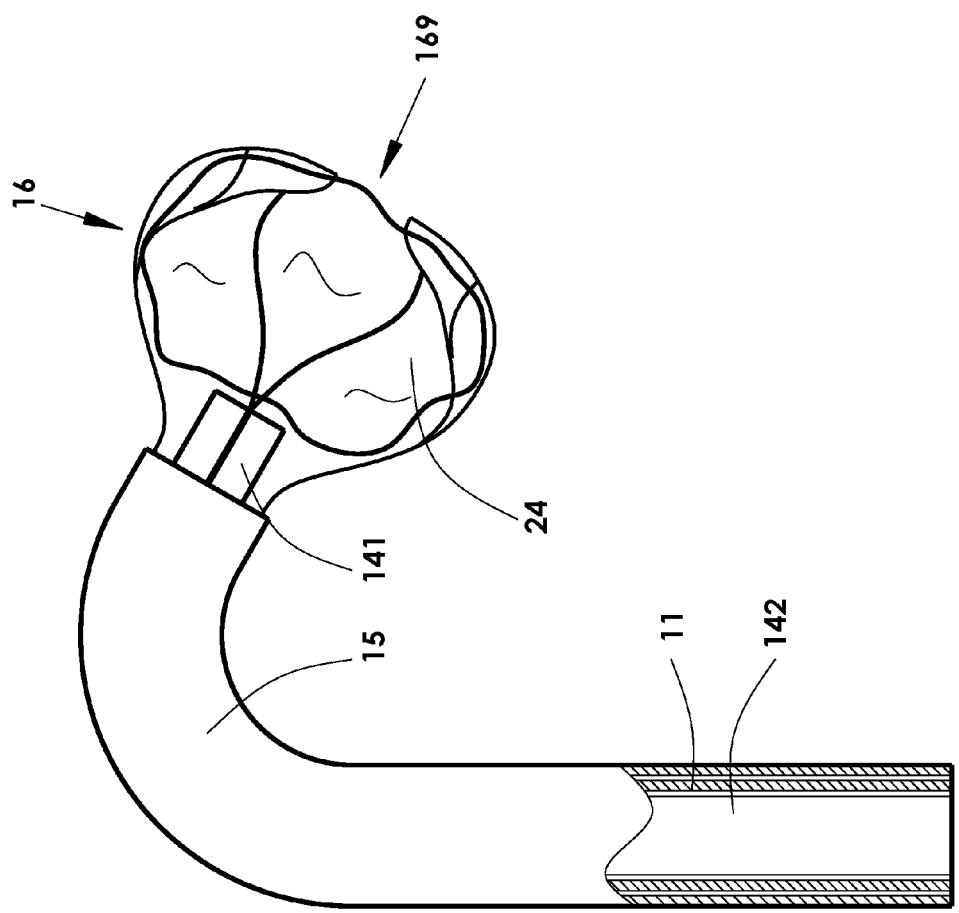
FIG. 2C illustrates a schematic side elevational view, partially broken away, of a distal portion of the medical device shown in FIG. 1, showing a foreign object being entrapped inside the basket.

FIG. 2C illustrates an example of operation of the medical device shown in FIG. 1 when an object (concretion) 21 is entrapped inside the retrieval basket 16. Depending on the lithotripsy technique, the end of the impact tip 141 of the lithotripsy probe can be brought to be close to, or in direct contact with a surface of the object 21. Then, the lithotripsy probe 14 is energized for breaking the concretion into much smaller fragments. Large fragments of the concretion are retained in the basket, while, at least in the case of kidney stones, smaller fragments may escape from the basket, and subsequently pass out of the body with the urine. Finally, removal of the sheath 15 together with the endoscope will enable the whole device to be removed from the body organ together with the object immobilized within the basket.

The entire medical device of the present invention may be constructed in a number of sizes and lengths, so as to be able to pass through the various sizes of ducts and cavities of a living body and the various dimensions of working channels of commercial cystoscopes, ureteroscopes or other endoscopes.

Generally speaking, the overall axial length of the device of the present invention can, for example, be in the range of from about 1 m to about 3 m. Shorter or longer overall lengths are also contemplated as may be required to effect a particular procedure.

It should be understood that the overall diameter of the cross-section of the medical device of the present invention should in use be small enough to accommodate any working channel through which the device of the invention is used. Specifically, the overall diameter of the cross-section of the lithotripsy probe 14 depicted in FIGS. 1, 2A and 2B can, for example, be from about 0.2 mm to about 2 mm. It will be understood that the inner diameter of the tubular member 11 should be great enough to provide axial movement of the lithotripsy probe 14 within the lumen 13. The outer diameter of the tubular member 11 can, for example, be in the range of from about 0.3 to about 2.5 mm, whereas the outer diameter of the tubular member 11 at the joining portion 166, where the filament strands are attached to the tubular member 11, can be in the range of from about 0.4 mm to about 2.8 mm.

The inner diameter of the dilator sheath 15 can, for example, be in the range of from about 0.4 to about 3 mm, whereas the outer diameter of the dilator sheath 15, can be in the range of from about 0.44 to about 3.5 mm.

For example, when the outer cross-sectional diameter of the dilator sheath 15 is 1.00 mm (3Fr) or smaller the entire medical device of the present invention may be used together with the commercial ureteroscope DUR-8 (available from ACMI) that has dimensions of the working channels of 1.2 mm (3.6 Fr).

Figure 3:
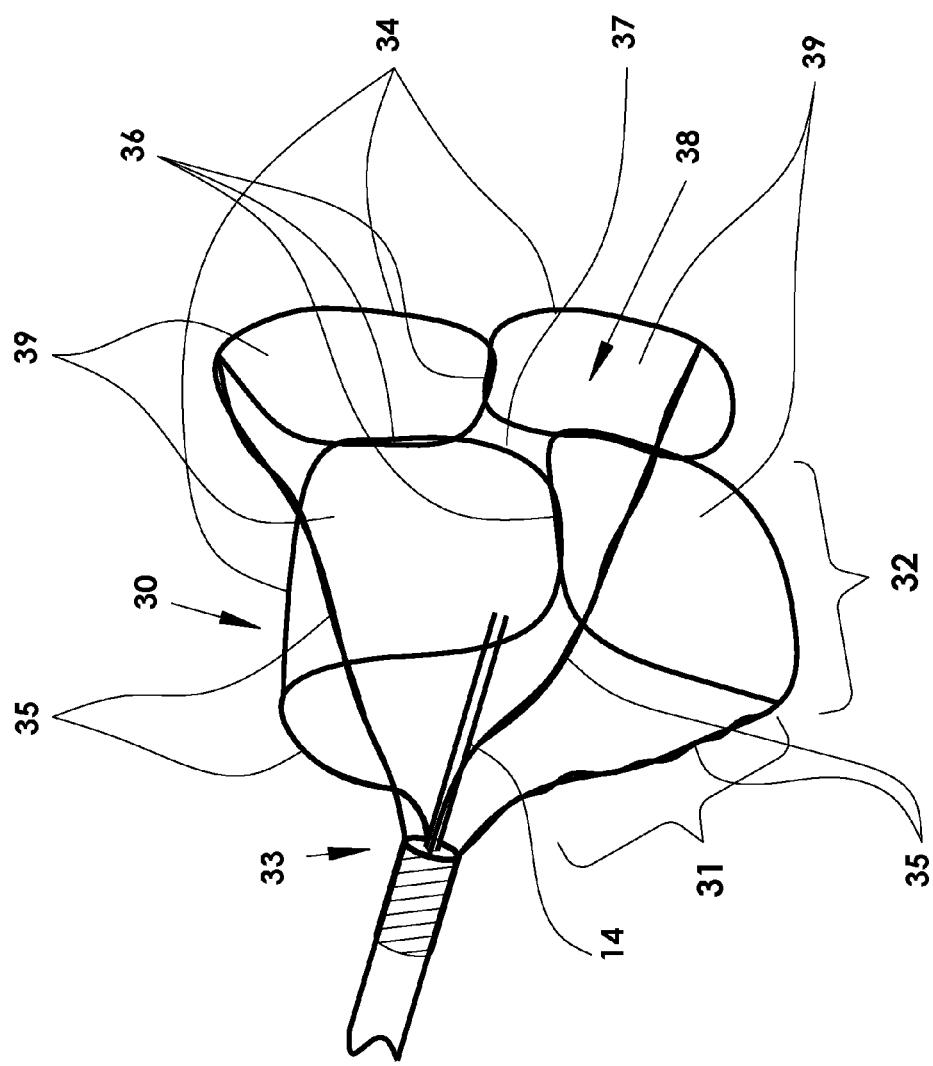
FIG. 3 illustrates a plan view of a distal portion of a medical device of the present invention having a retrieval basket according to one embodiment of the present invention.
Figure 4:
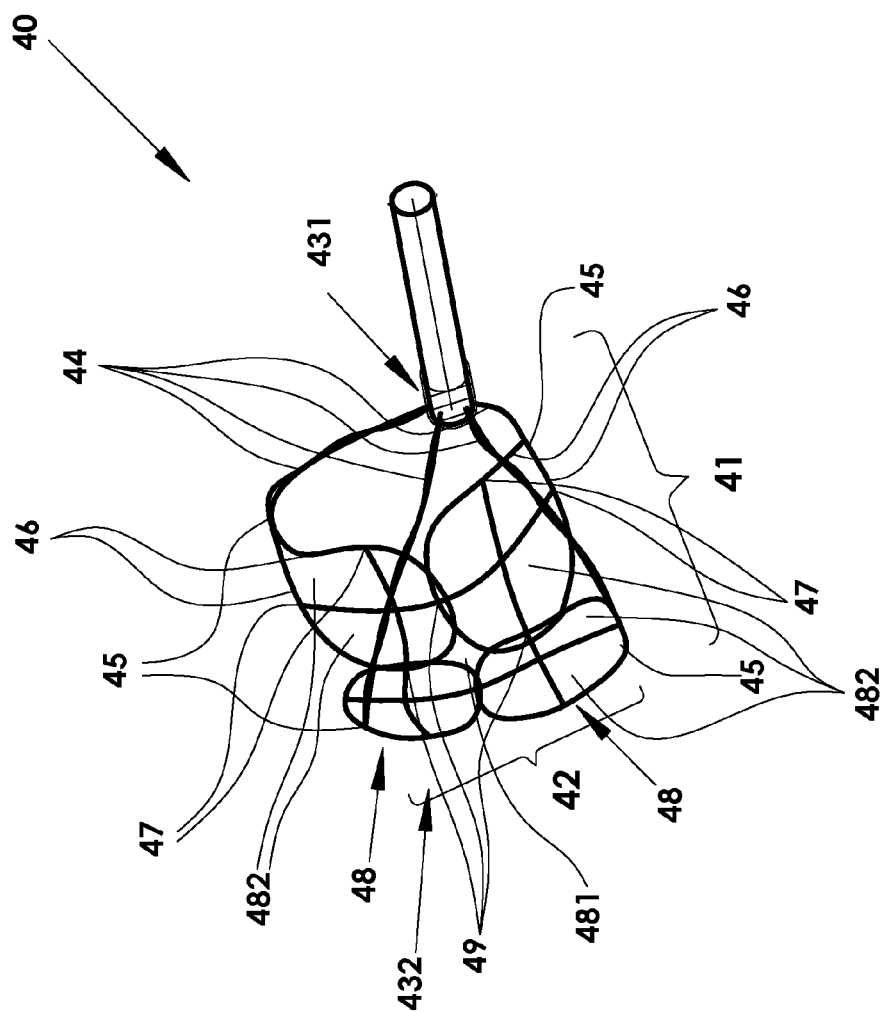
FIG. 4 illustrates a plan view of a distal portion of a medical device of the present invention having a retrieval basket according to another embodiment of the present invention.
Figure 5:
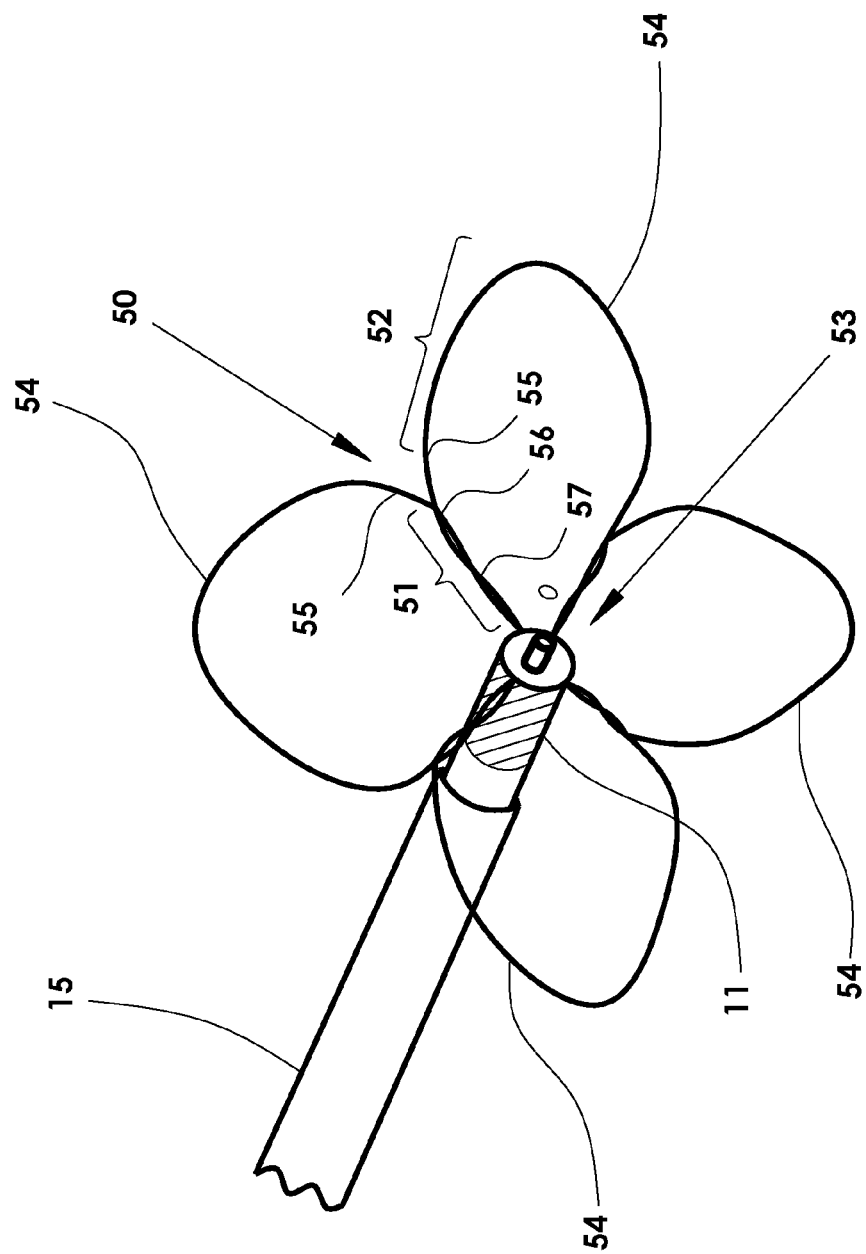
FIG. 5 illustrates a plan view of a distal portion of a medical device of the present invention having a retrieval basket according to a further embodiment of the present invention.

Referring now to FIGS. 3-5, various configurations of the retrieval basket 16 will be described hereinbelow.

FIG. 3 shows a plan view of a distal portion of a medical device of the present invention having a retrieval basket 30 for entrapping and retaining a foreign object (not shown) in a deployed position, according to one embodiment of the present invention. The structure of the retrieval basket 30 comprises a proximal portion 31 and a distal portion 32. The structure is constituted by a plurality of filaments that originate from a basket proximal end 33 of the proximal portion 31, then extend towards the distal portion 32, and finally return to the end 33, thereby forming a plurality of filament loops 34 in the distal portion 32, and a plurality of filament strands 35 in the proximal portion 31. In accordance with the embodiment shown in FIG. 3, each filament strand 35 is formed by twisting the same filament that extends from the end 33 towards the distal portion and then returns to the end 33 after forming the corresponding wire loop 34.

In the distal portion 32, each side of each wire loop 34 is directly connected to a side of an adjacent loop. According to one embodiment of the invention, connection 36 of the sides of the loops 34 in the distal portion 32 is achieved by twisting each pair of the filaments forming the corresponding sides of the neighboring loops 34 by one or more turns. Likewise, the connection 36 of the sides of the neighboring loops can also be achieved by soldering, brazing, gluing, etc. Connecting the sides of the loops provides structural rigidity and dilatation ability to the basket.

The filament loops 34 define a net that has a distal opening 37 at a basket distal end 38, where the loops 34 are not bound, and a plurality of side openings 39 along the basket's structure. The distal opening 37 in the basket has such dimension so that to permit the lithotripsy probe 14 to be protruded through the distal opening 37, when desired. In turn, the side openings 39 are configured for enabling the relatively small concretions to pass through to be captured and entrapped within the basket.

Referring to FIG. 4, there is shown a plan view of a distal portion of a medical device of the present invention having a retrieval basket 40 for entrapping and retaining a foreign object (not shown) in a deployed position, according to another embodiment of the present invention. The structure of the retrieval basket 40 comprises a proximal portion 41 and a distal portion 42. The structure is constituted by a plurality of filaments that originate from a basket proximal end 431 and are bound together at the proximal portion 41 to form a plurality strands 44 (four strands are shown in FIG. 4). In the distal portion 42 the strands 44 ramify at branching points 45 into sub-strands 46, which in turn ramify at branching points 47. After ramification of the strands 44 and the sub-strands 46, the filaments form a plurality of filament loops 48 (four filament loops are shown in FIG. 4). Sides of each loop 48 are connected to the sides of two adjacent neighboring loops. The places of connections are indicated by a reference numeral 49. The connection of the sides of the loops 48 can, for example, be achieved by twisting the filaments forming the corresponding sides of the neighboring loops by one or more turns. Likewise, the connection of the sides of the neighboring loops can also be achieved by soldering, brazing, gluing, etc.

The filament loops 48 define a net that has a distal opening 481 at a basket distal end 432, where the loops 34 are not bound, and a plurality of side openings 482 along the basket's structure. The distal opening 481 in the basket has such dimension so as to permit the lithotripsy probe (not shown in FIG. 4) to be protruded through the distal opening 481, when desired. In turn, the side openings 482 are configured for enabling the relatively small concretions to pass through to be captured and entrapped within the basket.

Referring to FIG. 5, there is shown a plan view of a distal portion of a medical device of the present invention having a retrieval basket 50 for entrapping and retaining a foreign object (not shown) in a deployed position, according to a yet another embodiment of the present invention. According to this embodiment, the structure of the retrieval basket 50 has a petal shape and comprises a proximal portion 51 and a distal portion 52. The structure is formed by a plurality of filaments that extend from an end 53 of the proximal portion 51 towards the distal portion 52 and then return to the end 53 to form a plurality of filament loops 54. In the proximal portion 51, each side 55 of each loop 54 is directly connected to a side 55 of an adjacent loop 54 at one or more points between the end 53 and a distal connection point 56. Specifically, each side 55 of each loop 54 is connected to a side of an adjacent loop at continues length sections, thereby forming a plurality of strands 57 at the basket proximal portion. This feature provides structural rigidity and dilatation ability to the basket. However, the loops 54 are not interconnected in the distal portion 52. Specifically, the loops 54 deploy radially outward and away from each other in the distal portion 52 when the basket is deployed outside the dilator sheath 15.

According to one embodiment of the invention, the filament loops 54 are generally flat and planar. According to another embodiment of the invention, each side 55 of the filament loops is slightly bent or arcuate into an arc (C-shaped configuration). Such a configuration can enhance the ability to slip the loops over the foreign object and grasp it. According to still another embodiment of the invention, each side 55 of the filament loops 54 is slightly undulated into a somewhat S-shaped configuration. Such a configuration can facilitate retraction of the basket into the sheath 15.

According to one embodiment of the present invention, the connection of the sides 55 of the loops 54 in the proximal portion 51 is achieved by twisting each pair of the corresponding sides 55 by one or more turns and forming twisted parts of the strands 57. Likewise, the connection of the sides of the neighboring loops can also be achieved by soldering, brazing, gluing, etc.

From the foregoing description it should be appreciated that retrieval baskets of the medical device constructed in accordance with the present invention, can comprise a variety of user desired shapes, number of loops, shape of the loops, types of connection of the loops in the proximal portion and types of connection of the loops to a manipulation rod. Thus, although the exemplary baskets 30, 40 and 50 having four filament loops 34, 48 and 54 are illustrated in FIGS. 3-5, respectively, showing the baskets in accordance with different embodiments, the invention is not limited by such basket structures. Generally, any desired number of the loops equal to or greater than two may be fabricated, mutatis mutandis.

Turning now to FIGS. 6A, 6B, 7, 8 and 9, various types of the lithotripsy probe 14 suitable for the purpose of the present invention will be described hereinbelow.

According to one embodiment of the invention, the lithotripsy probe 14 provides energy of a shock-wave of electrohydraulic lithotripsy (EHL). FIG. 6A shows schematically the impact tip 141 of the lithotripsy probe 14 used in EHL, and location of a concretion 61 juxtaposed against the impact tip 141. The impact tip 141 includes a high voltage central electrode 62, which is surrounded by an annular electrode 63, formed as a tubular member concentric with the central electrode 62. The object 61, e.g., a calculus, is distant from both electrodes 62 and 63, and due to a gap 64 none of the electrodes is in direct electrical contact with the object 61. The energy unit 143 includes an EHL pulse generator (not shown) coupled to the central electrode 62 and the annular electrode 63 via the control cable 142.

In operation, a series of high voltage pulses of sufficiently short duration, to avoid harm to human tissues, is generated in an electrical pulse generator (not shown). Pulses therefrom are directed to the impact tip 141 to produce a spark discharge between the electrodes 62 and 63. Shock waves 65 produced by the spark discharge propagate towards the concretion 61 through the gap 64 and break it into peaces. It should be noted that no discharge channel is formed within the calculus itself.

Various EHL pulse generators are commercially available. Examples of commercially available EHL generators include, but are not limited to, Karl Storz 27080 system, Model 2137 from Richard Wolf, GmbH, etc.

According to another embodiment of the invention, the lithotripsy probe 14 is based on electro-impulse destruction. The lithotripsy probe 14 used in electro-impulse destruction can be similar to the lithotripsy probe used in EHL, which is shown in FIG. 6A. The difference between electro-impulse destruction and the EHL destruction is in the mutual arrangement of the probe and object and in the slope of the voltage pulse utilized for spark discharge. FIG. 6B shows schematically the location of the object 61, with respect to the impact tip 141 at electro-impulse destruction. In this case, at least one of the electrodes 62 and 63 (or both electrodes 62 and 63) is (are) placed directly on the object surface to locate the spark discharge within the bulk of the object 61. Due to this provision the high voltage spark discharge produces spark channel within the object itself. Due to release of impulse energy within the spark channel the pressure within the channel dramatically increases, diameter of the channel enlarges causing tensile stresses within the object. The object can be efficiently fragmented and destroyed due to these tensile stresses in combination with hydraulic pressure of the surrounding liquid medium and collisions with the fragments of the object.

It should be understood that the lithotripsy probe 14 is not bound by any specific configuration of the electrodes 62 and 63. For example, the annular electrode 63 can be combined with miniaturized grasping forceps configured for grasping the foreign body anywhere along its length as described in U.S. Pat. No. 7,087,061 to Chernenko, et al., the disclosure of which is incorporated hereby by reference into this description.

In practice, for calculi appearing in a living body that have dimensions in the range of from about 3 mm to several centimeters, the electrical pulses supplied to electrodes can be defined by the following parameters: rise time of the pulse front is less than about 100 nanoseconds, preferably less than about 40 nanoseconds; duration of the pulse is less than about 5 microseconds, preferably 0.5-0.3 microseconds, pulse energy is in the range of about 0.1-1 Joule, impulse amplitude is in the range of about 5-30 kV. The preferred configuration of the pulses is rectangular.

Figure 7:
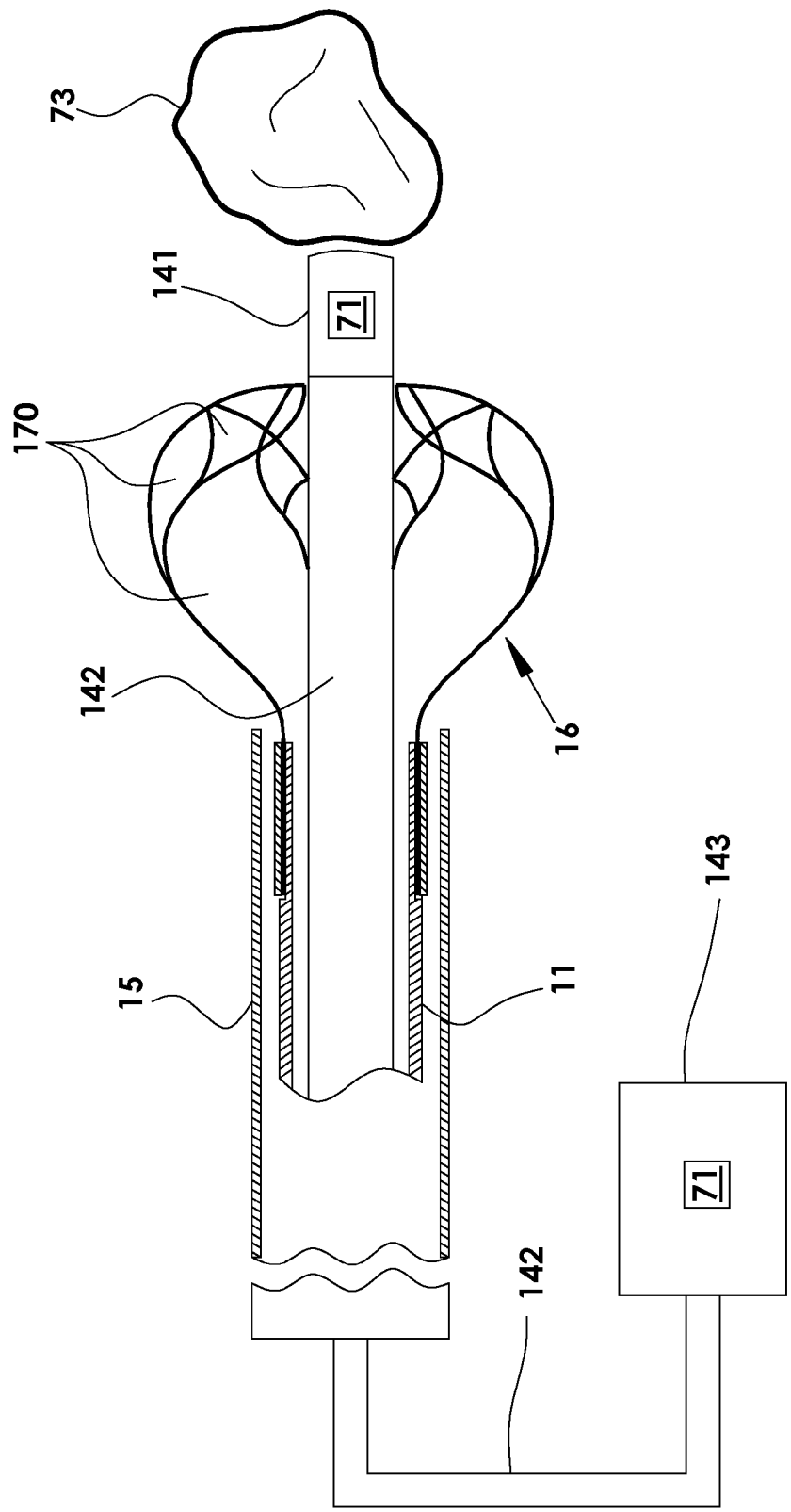
FIG. 7 illustrates schematically the juxtaposition of the concretion and the impact tip of the ultrasonic lithotripsy probe.

Referring to FIG. 7, according to a further embodiment of the invention, the lithotripsy probe 14 provides energy of ultrasonic wave for breaking concretions. In this case, the lithotripsy probe 14 includes an ultrasonic-vibration generation source 71 mounted either in the energy unit 143 or in the impact tip 141, and adapted for irrigation fluid near the impact tip 141. When the ultrasonic-vibration generation source is mounted in the energy unit 143, the control cable 142 can include an ultrasonic transmission line for transferring the ultrasonic energy to the tip 141. In operation, the tip 141 is juxtaposed against the concretion 73. At the tip, an ultrasonic wave formed by the probe 14 is directed towards the concretion 73.

It should be noted that the present invention is not limited to any specific implementation of the ultrasonic probe. Examples of ultrasonic probes suitable for the purpose of the present invention are described in U.S. Pat. No. 4,046,150 to Schwartz, et al.; U.S. Pat. No. 5,403,324 to Ciervo, et al.; and U.S. Pat. No. 6,613,056 to Brumbach, et al., the disclosure of which is incorporated hereby by reference into this description.

Figure 8:
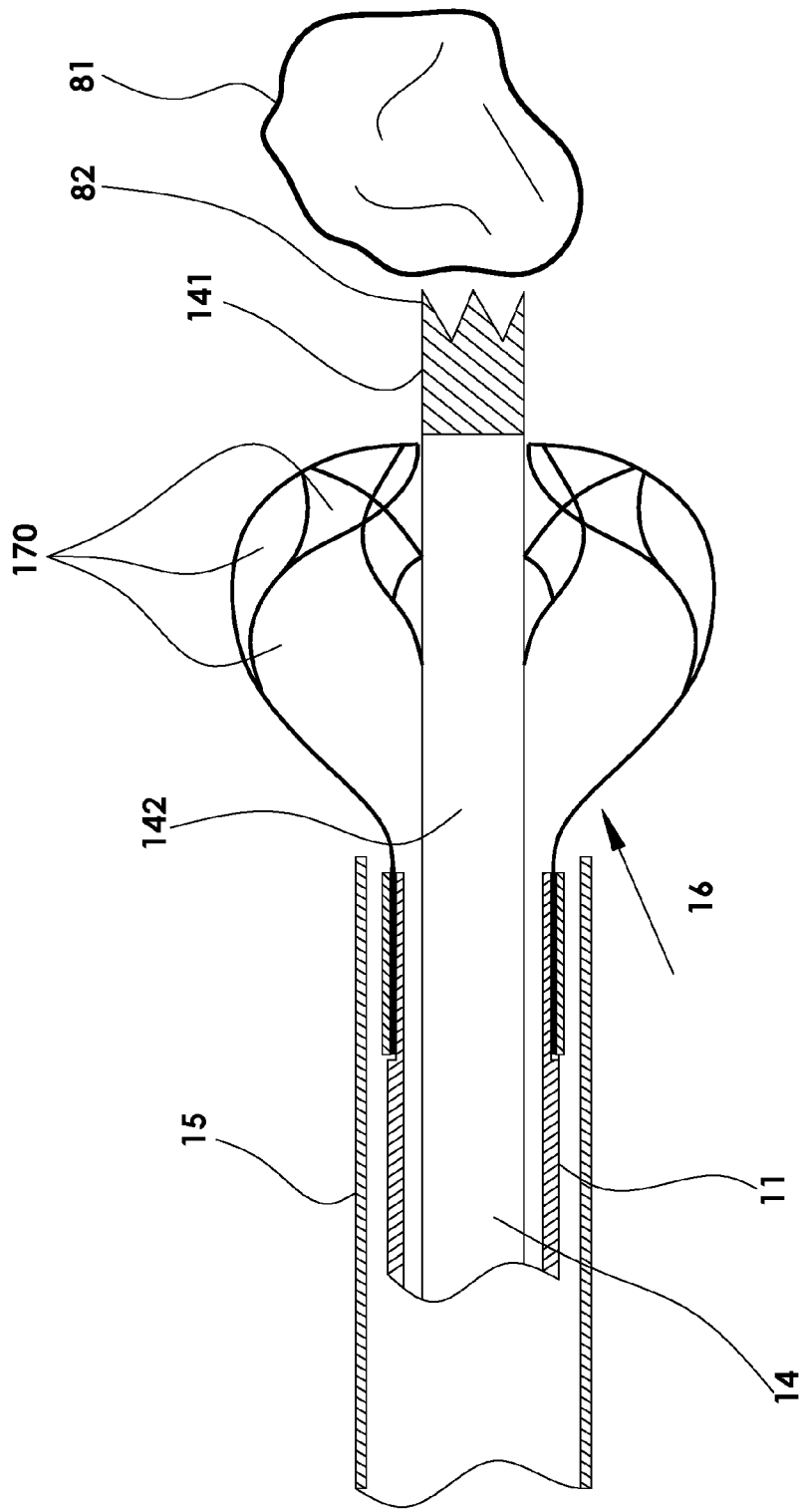
FIG. 8 illustrates schematically the juxtaposition of the concretion and the impact tip of the mechanical lithotripsy probe.

Referring to FIG. 8, according to yet another embodiment of the invention, the lithotripsy probe 14 provides mechanical energy for breaking concretions. In this case, the control cable 142 of the lithotripsy probe 14 includes or represents a relatively stiff rod with the tip of the rod placed against the concretion 81. The rod is adapted for reciprocal movement between axially advanced and retracted positions for breaking the concretion into smaller pieces for easier removal from the body (not shown) in the retrieval basket. When desired, the energy unit 143 can include means (not shown) for moving the rod back and forth to impact the tip upon the concretion with a hammering action. Such means are known per se (see, for example, U.S. Pat. No. 5,176,688 to Narayan, et al., the disclosure of which is incorporated hereby by reference into this description), and therefore will not be expounded hereinbelow. When desired, the end of the tip 141 can include one or more cutting teeth 82 for facilitation of the shattering function.

Figure 9:
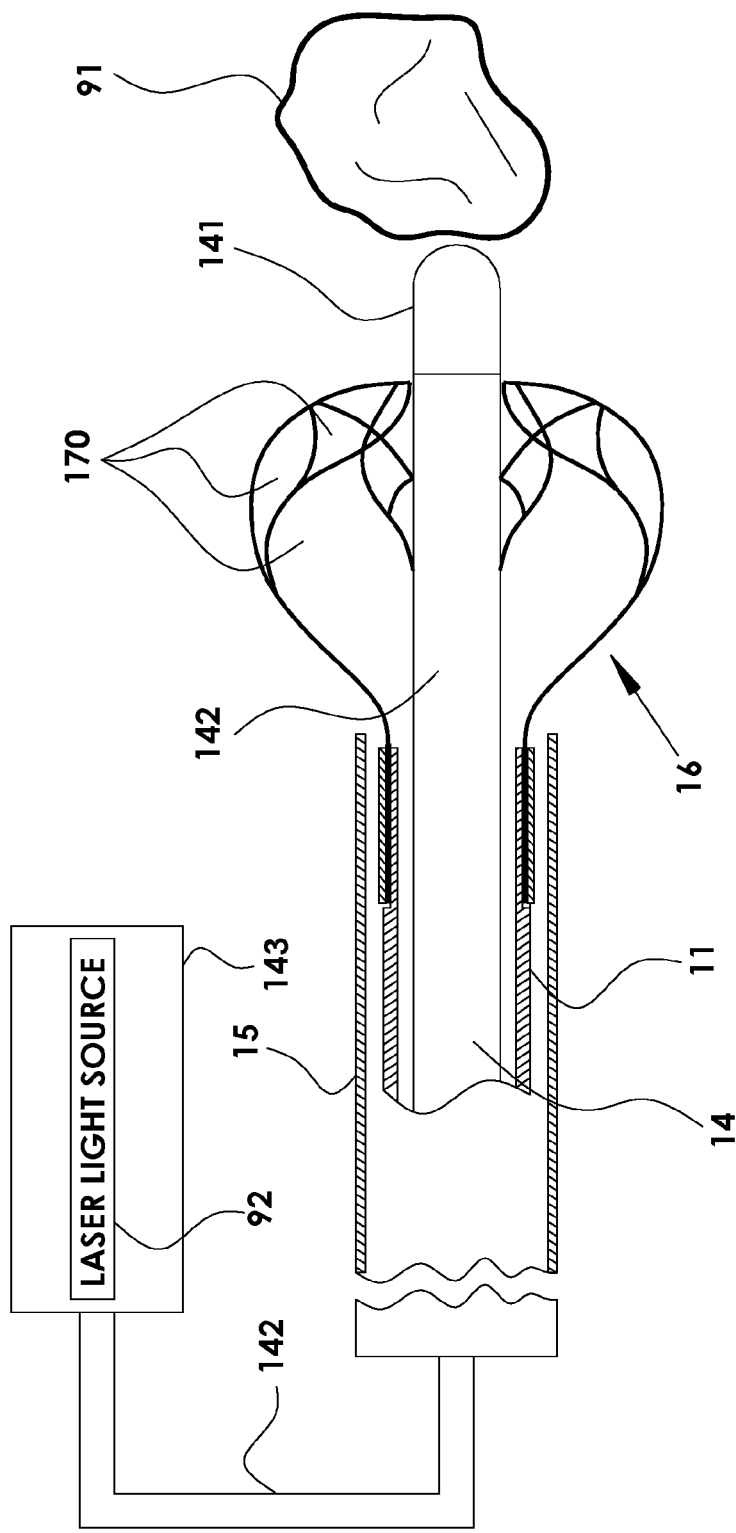
FIG. 9 illustrates schematically the juxtaposition of the concretion and the impact tip of the laser lithotripsy probe.

Referring to FIG. 9, according to yet another embodiment of the invention, the lithotripsy probe 14 provides energy of laser light for breaking a concretion 91. In this case, the lithotripsy probe 14 includes a laser light source 92 mounted in the energy unit 143. The lithotripsy probe 14 includes also a laser light guide mounted in or represented by the control cable 142. The laser light source 92 operates at a predetermined frequency that is preferably selected to match a peak absorption value of either the concretion or liquid in the vicinity of the concretion. The laser light emitted from the tip 141 and directed towards the concretion 91 can be absorbed by either the concretion or the liquid, thereby providing micro-explosions leading to concretion destruction. Examples of laser light probes suitable for the purpose of the present invention are described in U.S. Pat. No. 4,887,600 to Watson, et al.; U.S. Pat. No. 5,059,200 to Tulip; U.S. Pat. No. 5,041,121 to Wondrazek, et al., the disclosure of which is incorporated hereby by reference into this description.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that when desired the lithotripsy probe suitable for the purpose of the present invention can be a combination of any two or more lithotripsy techniques described above.

It should be understood that the medical device of the present invention is not limited to a medical treatment of a human body. It can be successfully employed for medical treatments of animals as well.

Moreover, the present invention is not limited to fabrication of medical devices, thus the apparatus of the invention can be used to shatter and extract any type of article from a wide range of inaccessible locations such as inside a pipe or tube (for example, the waste outlet of a domestic sink) or inside a chamber within a large piece of machinery which would be difficult to dismantle.

Also, it is to be understood that the phraseology and terminology employed herein are for the purpose of description and should not be regarded as limiting.

In the method claims that follow, alphabetic characters used to designate claim steps are provided for convenience only and do not imply any particular order of performing the steps.

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

What is claimed is:

1. A medical device for breaking a concretion in a body into smaller pieces and removing the pieces from the body, comprising:
   a dilator sheath adapted to penetrate into a passage of the body to reach the location where the concretion to be shattered into smaller pieces is located;
   a lithotripsy probe configured for shattering the concretion into smaller pieces;
   a tubular member located within the dilator sheath and being not a part of the lithotripsy probe, the tubular member having a tubular member proximal end, a tubular member distal end and an axially extending inner lumen provided within the tubular member to permit the entire lithotripsy probe to be inserted into the tubular member from the proximal end; and
   a retrieval basket coupled to said tubular member at the tubular member distal end, and configured for entrapping and retaining the concretion and the smaller pieces for their extraction from the body, said retrieval basket comprising a structure having a basket proximal portion and a basket distal portion, and constituted by a plurality of filaments extending from a basket proximal end towards a basket distal end, and then returning to the proximal end after forming a plurality of filament loops in the basket distal portion, and a plurality of filament strands at the basket proximal portion, each filament strand at the basket proximal portion being formed by twisting the same filament after forming the corresponding filament loop.

2. The medical device of claim 1, wherein said retrieval basket is not a part of the lithotripsy probe.

3. The medical device of claim 1, wherein said tubular member distal end has a hollowed-out portion for connecting said tubular member to the filament strands of the retrieval basket along the surface circumference of said hollowed-out portion.

4. The medical device of claim 3, comprising a tube put on the filament strands at said hollowed-out portion.

5. The medical device of claim 4, wherein said tube is made of a thermo-shrinkable material.

6. The medical device of claim 1, wherein said tubular member is a deflectable tube made from a material selected from polyimide, nylon, and polyester.

7. The medical device of claim 1, wherein said lithotripsy probe is selected from an electro-hydraulic lithotripsy probe, an electro-impulse lithotripsy probe, an ultrasonic wave lithotripsy probe, a mechanic lithotripsy probe, and a laser light lithotripsy probe.

8. The medical device of claim 1, wherein sides of the filament loops are overlapped or interlaced to provide a connection with each other so as to form a net defining a distal opening at the basket distal end and a plurality of side openings along the structure of the basket; said distal opening in the basket has such dimension so that to permit the lithotripsy probe to be protruded through said distal opening.

9. The medical device of claim 8, wherein the connection of the loops is achieved by twisting the filaments forming the corresponding sides of the adjacent loops by at least one turn.

10. The medical device of claim 1, wherein at the basket proximal end, the filament strands are connected to said tubular member along the surface circumference of said tubular member distal end.

11. The medical device of claim 1, wherein the filaments forming the structure of the basket are made of a metallic material having super elastic and thermo-mechanical shape memory characteristics.

12. The medical device of claim 11, wherein the metallic material is selected from NiTi based alloys and stainless steel.

13. The medical device of claim 11 wherein the metallic material includes a radiopaque material.

14. The medical device of claim 1 wherein said filaments are made of a core tube containing an axially disposed radiopaque wire.

15. The medical device of claim 1 comprising at least one radiopaque marker attached to at least one loop in said distal portion.

16. The medical device of claim 1, wherein the filaments forming the structure of the basket are multiwire strands.

17. The medical device of claim 16 wherein said multiwire strands include a central core wire and at least one another wire twisted about said central core wire, said another wire being made of a material having a level of radiopacity greater than the level of radiopacity of said central core wire.

18. The medical device of claim 1 wherein the filaments are made of non-metallic material.

19. A method for breaking a concretion in a body it into smaller pieces and removing the pieces from the body by using a medical device comprising:
   a dilator sheath adapted to penetrate into a passage of the body to reach the location where the concretion to be shattered into smaller pieces is located;
   a lithotripsy probe configured for shattering the concretion into smaller pieces;
   a tubular member located within the dilator sheath and being not a part of the lithotripsy probe;
   the tubular member having a tubular member proximal end, a tubular member distal end and an axially extending inner lumen provided within the tubular member to permit the entire lithotripsy probe to be inserted into the tubular member from the proximal end; and
   a retrieval basket coupled to said tubular member at the tubular member distal end, and configured for entrapping and retaining the concretion and the smaller pieces for their extraction from the body, said retrieval basket comprising a structure having a basket proximal portion and a basket distal portion, and constituted by a plurality of filaments extending from a basket proximal end towards a basket distal end, and then returning to the proximal end after forming a plurality of filament loops in the basket distal portion, and a plurality of filament strands at the basket proximal portion, each filament strand at the basket proximal portion being formed by twisting the same filament after forming the corresponding filament loop;

the method comprising:
- (a) inserting said medical device in a basket closed position through an endoscope into said body into proximity with the concretion;
- (b) manipulating the tubular member and the dilator sheath for opening the retrieval basket, entrapping the concretion in the retrieval basket, and closing the basket around the concretion;
- (c) manipulating said lithotripsy probe for protruding thereof from the lumen in the tubular member and bringing thereof into proximity with the concretion entrapped in the retrieval basket;
- (d) energizing said lithotripsy probe to cause the concretion to break into smaller pieces; and
- (e) removing the medical device from the body together with at least one smaller piece of the concretion immobilized within the basket.

20. A method for breaking a concretion in a body it into smaller pieces and removing the pieces from the body by using a medical device comprising:
- a dilator sheath adapted to penetrate into a passage of the body to reach the location where the concretion to be shattered into smaller pieces is located;
- a lithotripsy probe configured for shattering the concretion into smaller pieces;
- a tubular member located within the dilator sheath and being not a part of the lithotripsy probe;
- the tubular member having a tubular member proximal end, a tubular member distal end and an axially extending inner lumen provided within the tubular member to permit the entire lithotripsy probe to be inserted into the tubular member from the proximal end; and
- a retrieval basket coupled to said tubular member at the tubular member distal end, and configured for entrapping and retaining the concretion and the smaller pieces for their extraction from the body, said retrieval basket comprising a structure having a basket proximal portion and a basket distal portion, and constituted by a plurality of filaments extending from a basket proximal end towards a basket distal end, and then returning to the proximal end after forming a plurality of filament loops in the basket distal portion, and a plurality of filament strands at the basket proximal portion;

wherein sides of the filament loops are connected to the sides of adjacent loops at the distal portion of the basket to form a net defining a distal opening at the basket distal end and a plurality of side openings along the structure of the basket;

the method comprising:
- (a) inserting said medical device in a basket closed position through an endoscope into said body into proximity with the concretion;
- (b) manipulating said lithotripsy probe for protruding thereof from the lumen in the tubular member and the distal opening of the basket to bring said lithotripsy probe into proximity with the concretion entrapped in the retrieval basket;
- (c) energizing said lithotripsy probe to cause the concretion to break into smaller pieces;
- (d) manipulating the tubular member and the dilator sheath for opening the retrieval basket, entrapping at least one piece of the concretion in the retrieval basket, and closing the basket around the piece; and
- (e) removing the medical device from the body together with said at least one smaller piece of the concretion immobilized within the basket.

\* \* \* \* \*